US006638299B2

(12) United States Patent
Cox

(10) Patent No.: US 6,638,299 B2
(45) Date of Patent: Oct. 28, 2003

(54) CHIROPRACTIC TREATMENT TABLE AND METHOD FOR SPINAL DISTRACTION

(76) Inventor: James M. Cox, 2320 Fox Chase Run, Fort Wayne, IN (US) 46825

( * ) Notice: Subject to any disclaimer, the term of this patent is extended or adjusted under 35 U.S.C. 154(b) by 0 days.

(21) Appl. No.: 09/952,587

(22) Filed: Sep. 14, 2001

(65) Prior Publication Data

US 2003/0055456 A1 Mar. 20, 2003

(51) Int. Cl.[7] .................................................... A61F 5/00
(52) U.S. Cl. ............................ 606/243; 606/241; 5/617
(58) Field of Search ......................... 606/237, 240–245; 602/32, 33; 601/24, 39; 128/845; 5/617, 618, 620, 943

(56) References Cited

U.S. PATENT DOCUMENTS

| | | | | |
|---|---|---|---|---|
| 1,233,496 A | | 7/1917 | Nichols | |
| 3,343,531 A | | 9/1967 | Thompson | |
| 3,898,985 A | * | 8/1975 | Butcher et al. | 601/146 |
| 4,404,966 A | | 9/1983 | Hartman | |
| 4,649,905 A | | 3/1987 | Barnes | |
| 4,660,549 A | | 4/1987 | Kowalski et al. | |
| 4,724,828 A | * | 2/1988 | Barnes et al. | 606/245 |
| 4,732,141 A | | 3/1988 | Steffensmeier | |
| 5,060,636 A | | 10/1991 | Bell | |
| 5,192,306 A | * | 3/1993 | Scott et al. | 5/608 |
| 5,423,861 A | | 6/1995 | Kelley | |
| 5,569,166 A | * | 10/1996 | Stone | 601/21 |
| 5,954,750 A | * | 9/1999 | Steffensmeier | 606/237 |
| 6,077,293 A | | 6/2000 | King | |

OTHER PUBLICATIONS

Lloyd's Table Co. advertisement of Galaxy 900HS, Mar. 2001, Lloyd's Catalog.

* cited by examiner

*Primary Examiner*—Danton D. DeMille
*Assistant Examiner*—Quang D. Thanh
(74) *Attorney, Agent, or Firm*—George Pappas

(57) ABSTRACT

A chiropractic treatment table and method for treating a patient's spine for providing true longitudinal distraction alone or in combination with vertical flexion and extension, lateral flexion, and/or rotation. The treatment table includes a longitudinally moveable head support portion slidingly mounted on an anti-friction structure whereby the head support portion is freely moveable with practically no frictional or drag. In view of the anti-friction structure, the net longitudinal distraction force is primarily only that which is applied by the chiropractor thereby not requiring adjustment or compensation for drag or other forces, and thereby providing the chiropractor substantially improved control of the actual applied distraction force for administering the desired distraction.

30 Claims, 13 Drawing Sheets

CHIROPRACTIC TREATMENT TABLE AND METHOD FOR SPINAL DISTRACTION

TECHNICAL FIELD

The present invention relates to the technical field of chiropractic treatment tables and methods of treating a patient's spine. More particularly, the present invention relates to a chiropractic treatment table and treatment method of a patient's spine including the neck by using the treatment table and providing distraction as well as vertical flexion, extension, lateral flexion and rotational to the patient's spine.

BACKGROUND OF THE INVENTION

Chiropractic tables and various techniques or methods are today commonly used by chiropractors for treating a patient's spine including the neck. Treatments are provided for correcting and/or relieving discomfort as a result of various diseases, ailments and injuries including degenerative disc disease, facet arthrosis, stiffness, whiplash, headache, osteoporosis, muscle spasm, loss of mobility, etc. Such treatments include placing the patient's spine including the neck in vertical flexion (chin to chest motion), extension (head to back motion), lateral flexion (left and right motion) and rotation (turning) and coupling vertical and lateral flexion thereby providing circumduction.

Prior known tables which provide chiropractors the means to administer such treatments include those shown and described in Scott et al., U.S. Pat. No. 5,192,306 and Barnes U.S. Pat. No. 4,649,905. Scott et al., describes a chiropractic table wherein the headpiece is selectively pivotable about the table longitudinal axis, as well as vertical and horizontal axes located transverse to the longitudinal axis. Distraction is provided during vertical flexion when the table headpiece is rotated about the horizontal axis. In this regard, Scott et al., places the horizontal axis vertically above the thoracic cushion and coincident with the patient's spine whereby, upon pivotal motion of the headpiece downwardly about the horizontal axis, the neck is placed in flexion as well as distraction. Although this table provides many benefits, it is undesirable in that it is incapable of providing true distraction of the spine solely along the longitudinal axis and/or providing true distraction not as a result of flexion or rotational motion of the headpiece about the horizontal or vertical axes.

Barnes describes a similar chiropractic table wherein the headpiece is selectively pivotable about the table longitudinal axis, as well as vertical and horizontal axes located transverse to the longitudinal axis. Additionally, Barnes includes a rack and gear mechanism for selectively adjusting the longitudinal distance of the headpiece from the body support section and providing a traction mode of motion linearly and generally horizontally, and a stop mechanism for retaining the headpiece at a desired longitudinal distance from the body support section. Although the Barnes table provides for longitudinal motion of the headpiece, the structure thereof along with the rack and gear provide drag and make it difficult for the chiropractor to establish and administer the proper amount of distraction for the patient.

Accordingly, although prior chiropractic treatment tables and treatment methods provide for distraction of the spine they are insufficient in providing the chiropractor the desired control for properly administering distraction in a safe and beneficial manner.

SUMMARY OF THE INVENTION

It is the principal object of the present invention to overcome the disadvantages of prior chiropractic tables and treatment methods and provide the chiropractor the desired and necessary control for properly administering true longitudinal distraction alone as well as in combination with vertical and lateral flexion, extension, and rotation to the patient's spine.

The present invention overcomes the disadvantages associated with prior chiropractic treatment tables and methods and provides the chiropractor the desired and necessary control for properly administering true longitudinal distraction alone as well as in combination with vertical and lateral flexion, extension, and rotation to the patient's spine by providing a treatment table having a body support portion and a head support portion. The head support portion is mounted on the body support portion and is adapted for pivotal motion about a horizontal axis for providing vertical flexion and extension, about a vertical axis for providing lateral flexion, and about the table longitudinal axis for rotation. The head support portion is further supported on the body support portion with an anti friction structure making the head support portion selectively freely moveable relative to the body support portion along the longitudinal axis.

Preferably, the anti friction structure includes a slide block mounted between the head support portion and the body support portion. The slide block includes aligned upper and lower slide members selectively moveable parallel with one another and having anti friction bearings therebetween. A handle is mounted to the head support portion whereby the chiropractor can selectively move the head support portion as desired. An occipital restraint is preferably provided on the head support portion whereby a patient's head can selectively be restrained. A stop mechanism is also provided for selectively engaging the head support portion and preventing longitudinal movement thereof when only flexion therapy is desired.

By making the head support portion freely movable, the chiropractor is able to better feel and judge the distraction force being applied. That is, the anti friction structure provides very little drag to the longitudinal movement of the head support portion and, therefore, the net longitudinal distraction force is primarily only that which is being applied by the chiropractor. The chiropractor need not adjust or compensate for drag or other forces and, therefore, the chiropractor is substantially better able to control the actual applied force for administering the desired distraction. This control of the desired distraction is yet more beneficial and essential when the therapy being administered requires coupling longitudinal distraction with flexion and extension, about the vertical axis, lateral flexion about the horizontal axes and/or rotation about the longitudinal axis. As can be appreciated, during such therapy, the anti friction structure provides the chiropractor the necessary control for administering the desired proper distraction without having to adjust for drag or other forces. When using the treatment table, with or without the occipital restraint, one of the chiropractor's hands is preferably placed on the head support handle while the other is placed on the patient's neck or back. In this manner and with the anti friction structure, the actual applied distraction force is more accurately monitored and administered as desired.

Preferably, the method of treating a patient's spine includes first supporting the patient with the patient's body resting on the body support portion and the patient's head resting on the head support portion and, thereafter, selectively longitudinally moving the head support portion on the anti friction structure and the patient's head thereon, thereby selectively providing distraction to the patient's spine in a direction generally along the table longitudinal axis. Yet more preferably, the patient is supported in a generally face down position with a portion of the patient's face on the table head support portion and the occipital restraint placed on the patient's head for restraining the head thereon. Thereafter, by grasping the head support handle with one hand, the head support portion is selectively moved as needed for application of the desired therapy. The patient's neck and/or back can also be held by the chiropractor's other hand for monitoring and/or increasing the desired distraction. Additionally, the longitudinal distraction can be coupled with flexion by pivoting the head support portion about the vertical and horizontal axes and rotation about the longitudinal axis. For establishing the proper distraction to be applied, prior to actual application of distraction, the patient's tolerance is first tested by longitudinally moving the head support portion with only the weight of the patient's head thereon and, thereafter, by applying an occipital downward force on the patient's head while simultaneously longitudinally moving the head support portion thereby increasing the axial distraction force applied to the patient's spine.

In one form thereof the present invention is directed to a treatment table for treating a patient's spine while being supported in a generally face down horizontal position. The treatment table includes a first support portion supporting a patient's body, a second support portion supporting a patient's head and being spaced apart from the first support portion along a longitudinal axis. The second support portion is supported on an anti friction structure whereby the second support portion is selectively freely moveable relative to the first support portion along the longitudinal axis.

In one form thereof the present invention is directed to a treatment table for treating a patient's spine while being supported in a generally face down horizontal position. The treatment table includes a first support portion supporting a patient's body and a second support portion supporting a patient's head and being spaced apart from the first support portion along a longitudinal axis. The second support portion is supported on an anti friction mechanism for allowing generally free motion of the second support portion relative to the first support portion along the longitudinal axis.

In one form thereof the present invention is directed to a method of treating a patient's spine on a treatment table including a first portion adapted to support a patient's body and a second portion adapted to support the patient's head. The the second portion is selectively freely movable on an anti friction structure relative to the first portion along a longitudinal axis. The method includes the steps of supporting the patient with the patient's body resting on the first table portion and the patient's head resting on the second table portion, and selectively longitudinally moving the second table portion on the anti friction structure and the patient's head thereon, thereby selectively providing distraction to the patient's spine in a direction generally along the table longitudinal axis.

BRIEF DESCRIPTION OF THE DRAWINGS

The above-mentioned and other features and objects of this invention and the manner of obtaining them will become more apparent and invention itself will be better understood by reference to the following description of embodiments of the invention taken in conjunction with the accompanying drawings wherein.

Corresponding reference characters indicate corresponding parts throughout the several views of the drawings.

The exemplifications set out herein illustrate preferred embodiments of the invention in one form thereof and such exemplifications are not to be construed as limiting the scope of the disclosure or the scope of the invention in any manner.

DETAILED DESCRIPTION OF THE PREFERRED EMBODIMENT

Figure 1:
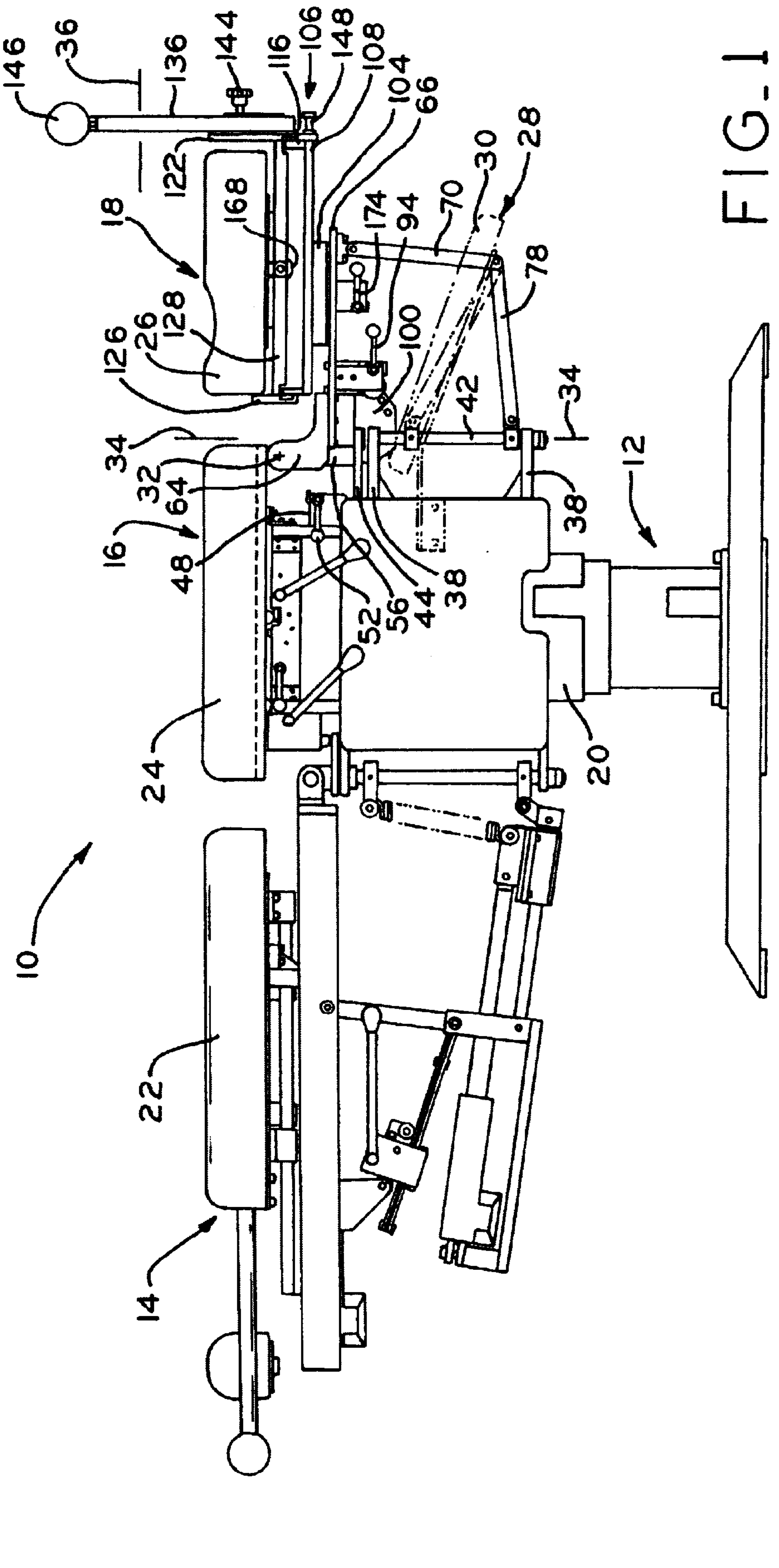
FIG. 1 is a side elevation view of a chiropractic treatment table constructed in accordance with the principles of the present invention.
Figure 2:
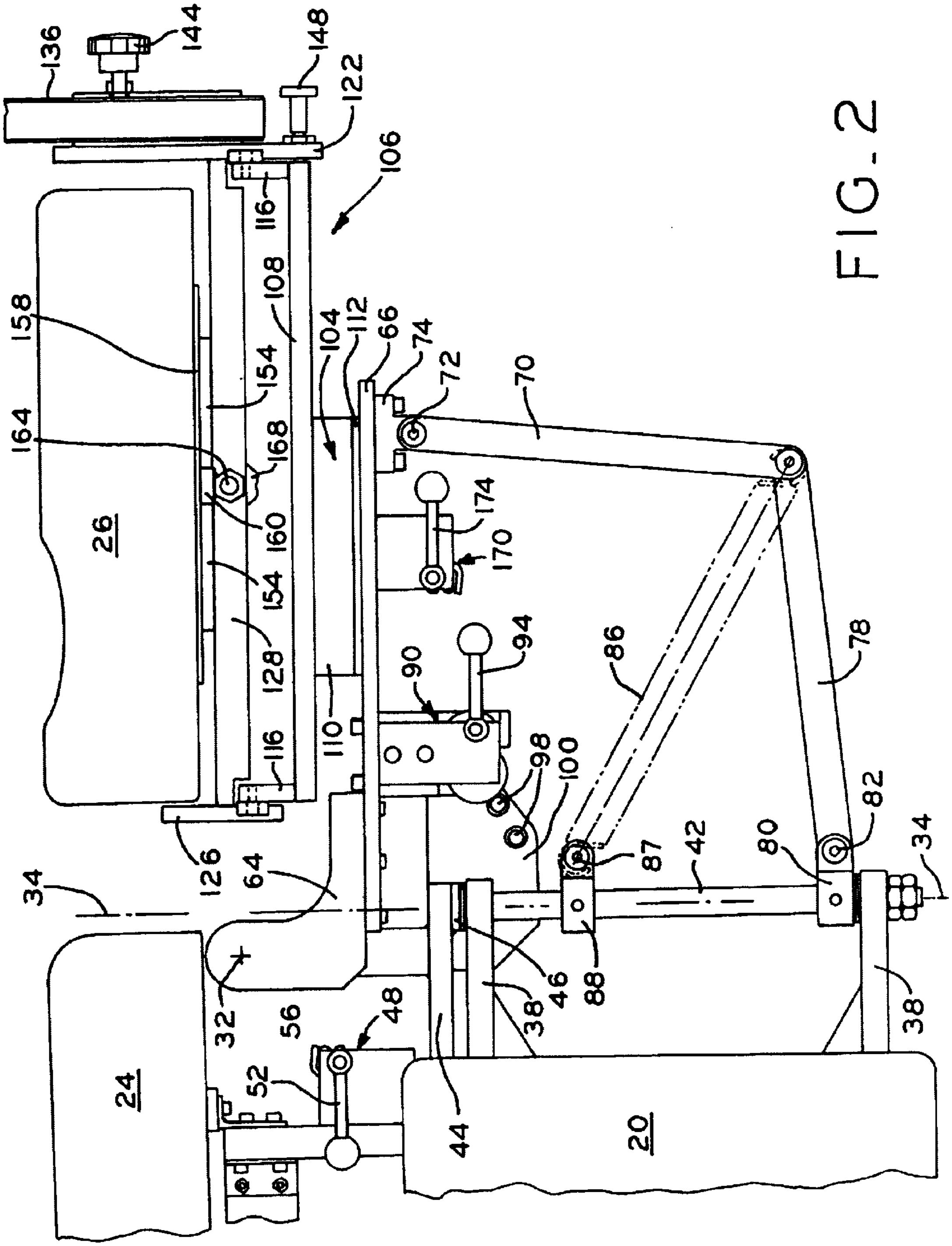
FIG. 2 is a side elevation view of the head support section of the table shown in FIG. 1.

Referring initially to FIG. 1, there is shown and generally designated by the numeral 10 a chiropractic treatment table constructed in accordance with the principles of the present invention. Treatment table 10 includes a base 12 supporting a legs support section 14, a body support section 16, and a head support section 18. Preferably, as shown, a pedestal 20 is supported on base 12 and the legs support section 14, body support section 16 and head support section 18 are mounted thereon. Treatment table 10 is adapted for use by a chiropractor standing adjacent thereto and for treatment of a patient lying face down in a prone position upon the treatment table 10. The patient is essentially supported on the table 10 with their legs and lower body on the lower cushion 22, their upper body on body cushion 24, and their head on the head rest cushions 26. In this position, the chiropractor manipulates the spinal vertebra as may be needed for providing the patient with the desired therapy.

As more fully discussed herein below, treatment table 10 is particularly well adapted for treatment of the vertebra in the cervical or neck area and, more particularly, for administering true longitudinal distraction alone as well as in combination with vertical and lateral flexion, extension and rotation. It is noted that during such treatment and while the patient is lying on the treatment table 10, the patient's arms are placed on the arm carriers 28, also mounted on the pedestal 20 and having arm cushions 30 thereon.

As more fully discussed herein below, the head support section or head piece 18 is selectively pivotable about a horizontal axis 32, a vertical axis 34, and about a longitudinal or table axis 36. It is noted that longitudinal axis 36 is above head rest cushions 26 and most preferably located so as to be generally collinear with the patient's cervical vertebra. More particularly, main support brackets 38 are attached to the pedestal 20 via screws 40. Main support brackets 38 pivotally support the main vertical rod member 42 and the main stop arm 44 which is attached to the rod member 42 at the upper end thereof. A thrust bearing 46 is provided around the rod member 42 and between the upper main support bracket 38 and the main stop arm 44. Accordingly, the vertical rod member 42, main stop arm 44, and the remaining head support section 18 is thereby pivotable about the main vertical rod member 42 or vertical axis 34.

Figure 3:
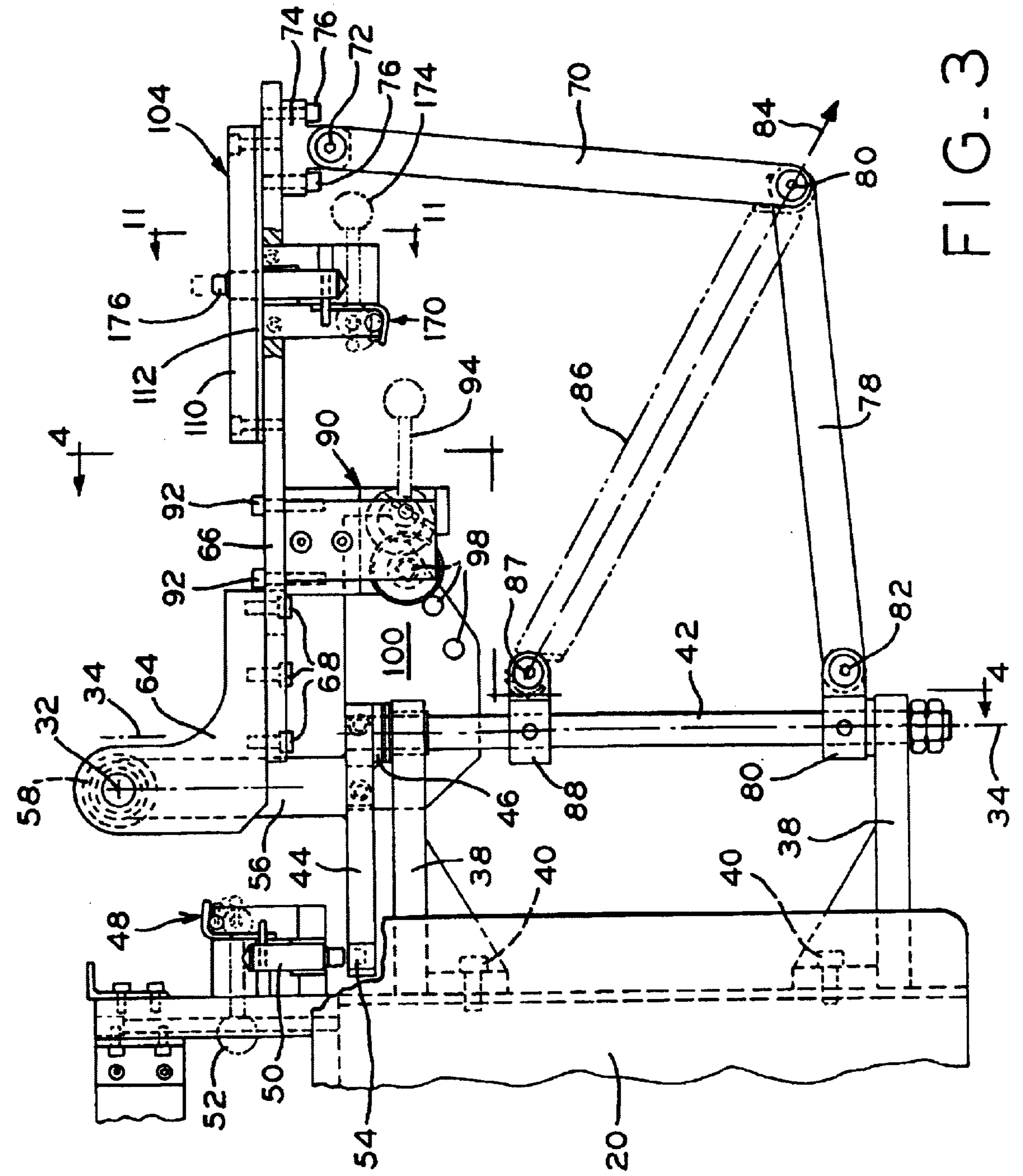
FIG. 3 is a side elevation view similar to FIG. 2 but with the head rest cushions removed and various components shown in dash lines.
Figure 4:
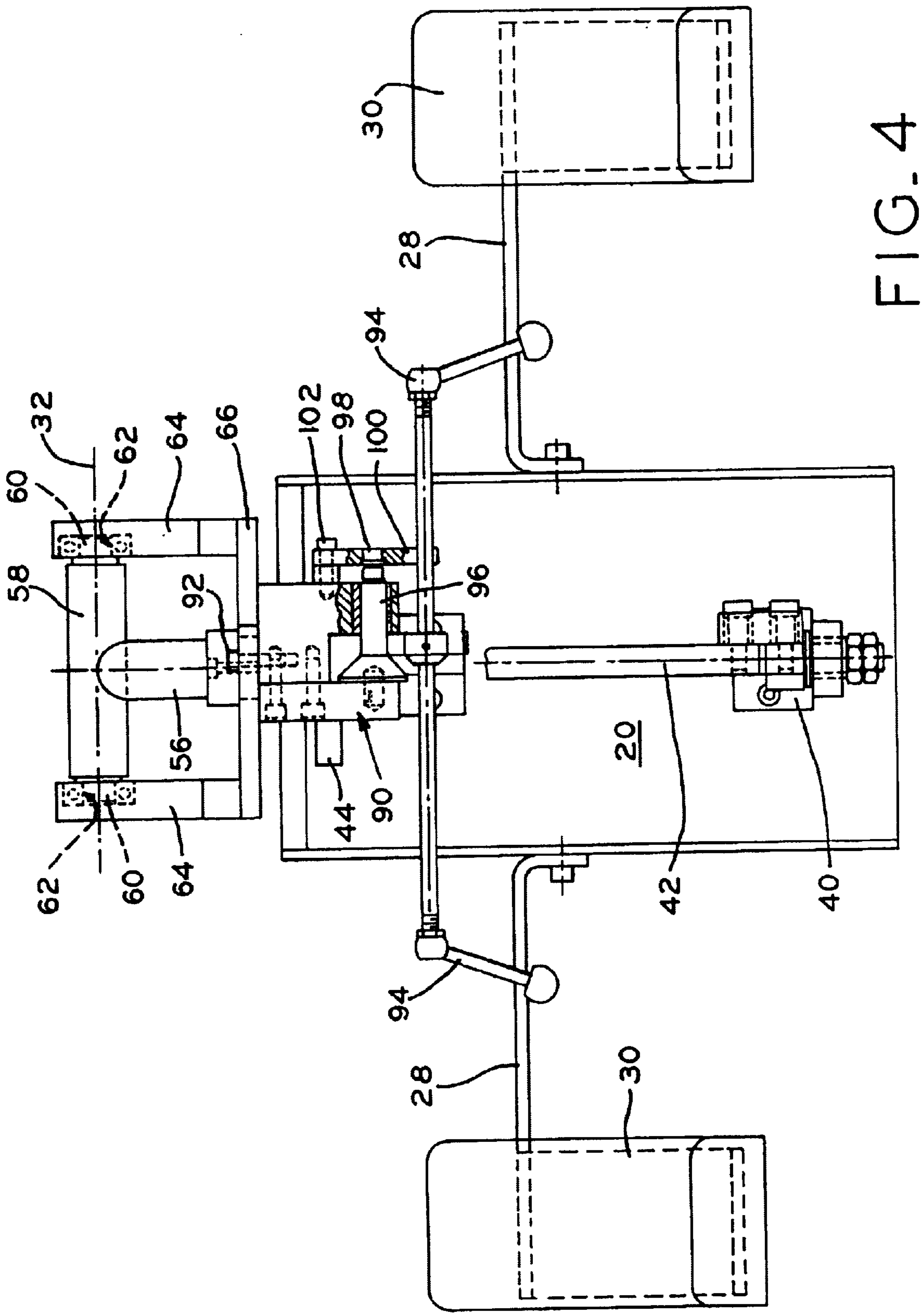
FIG. 4 is a cross-sectional view taken generally along line 4—4 of FIG. 3.
Figure 5:
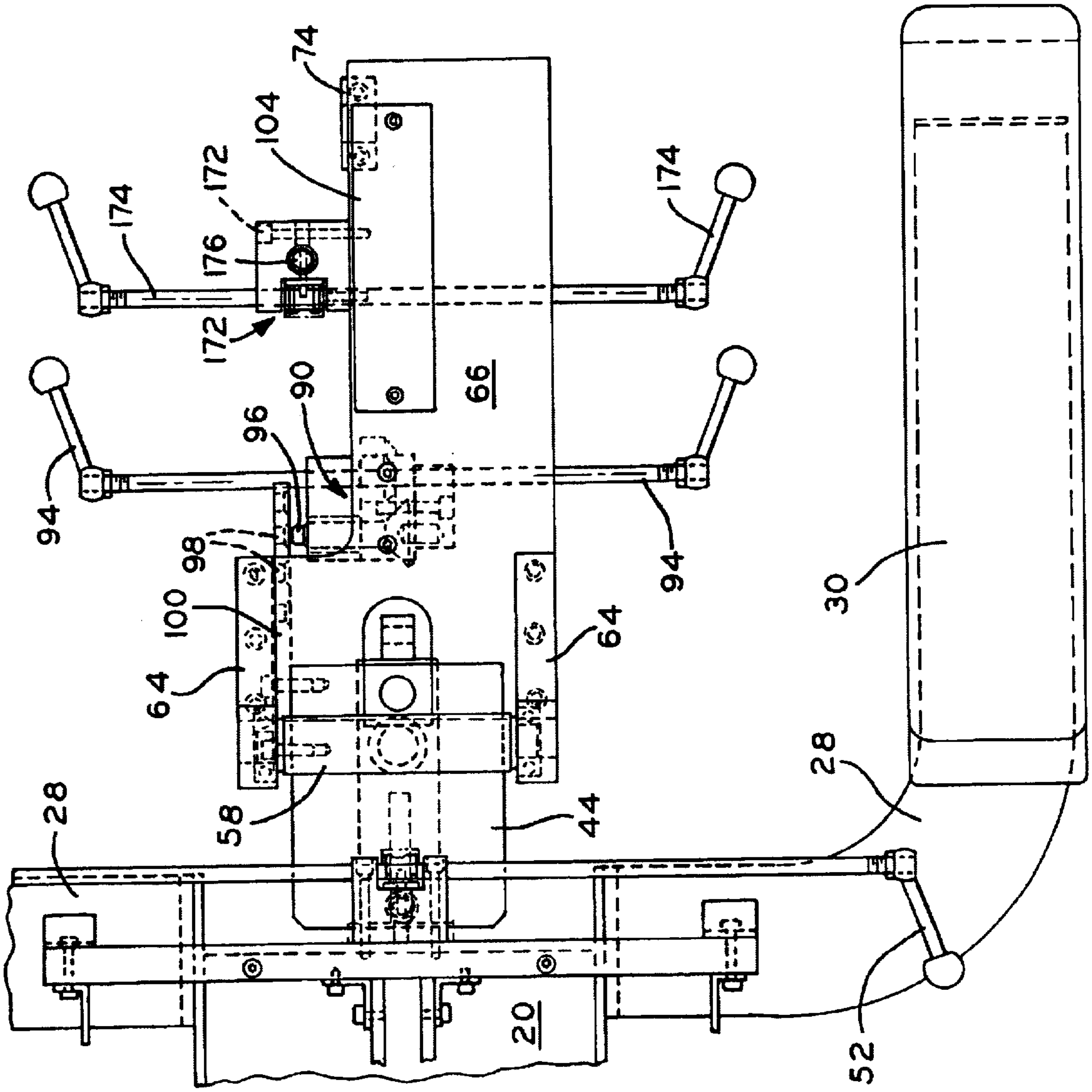
FIG. 5 is a top plan view of the head support section as shown in FIG. 3.

As best seen in FIG. 3, a cam mechanism 48 is attached to the pedestal 20 and is adapted to selectively move pin 50 vertically up and down by rotatably moving the handle 52. A pin receiving hole 54 is provided in the main stop arm 44, and pin 50 is adapted to be received within hole 54 when aligned therewith. Accordingly, by manipulating the lever handle 52 and selectively placing pin 50 within the pin receiving hole 54, the head support section 18 can selectively be fixed preventing lateral pivotal motion about the vertical axis 34 or, in the alternative, be freely laterally movable about the vertical axis 34 for providing lateral flexion.

A vertical extension 56 is affixed to the top of main stop arm 44 and extends vertically upwardly therefrom. A horizontal shaft 58 is affixed to the top of vertical extension 56 and the ends 60 thereof are pivotally received within holes 62 in L-shaped arms 64. Tongue 66 is affixed to each of the L-shaped arms 64 with screws 68. Accordingly, L-shaped arms 64 and tongue 66 are adapted to pivot about the horizontal axis 32 extending collinearly through the horizontal shaft 58.

An outer link 70 is pivotally attached with a screw bearing 72 to a mount 74 which is in turn affixed to the end of tongue 66 with screws 76. The lower end of outer link 70 is pivotally attached to the lower link 78 with a screw bearing 80. At its other end, lower link 78 is pivotally attached to the annular mount 80 with a screw bearing 82. As should now be appreciated, a parallelogram is formed with axes of rotation at horizontal axis 32 and screw bearings 72, 80 and 82 and, therefore, as tongue 66 is pivoted downwardly about horizontal axis 32, the pivotal connection between links 70 and 78 and the screw bearing 80 travel generally away from the pedestal 20 in a direction generally as indicated by arrow 84. A spring 86 is attached and extends between the screw bearing 80 and the screw bearing 87 of annular mount 88 which is affixed to the main vertical rod member 42. Spring 86 provides a force in the opposite direction to that of arrow 84 and, thereby, provides an upward force through outer link 70 to the tongue 66.

Tongue 66 and the head rest cushions 26 thereon can selectively be rotated about the horizontal axis 32 and fixed in different angular positions both vertically downwardly from the horizontal for vertical flexion and vertically upwardly from the horizontal for extension. In this regard, a cam mechanism 90 is provided and affixed to tongue 66 with screws 92. Cam mechanism 90 includes a lever handle 94 adapted to be turned and thereby cause pin 96 to selectively be moved horizontally within any one of the holes 98 in plate 100 which is affixed to the main stop arm 44 via screws 102. Thus, by turning lever handle 94 and retracting pin 96 from the holes 98, tongue 66 and the head rest cushions 26 supported thereon are selectively pivotable about the horizontal axis 32. However, by turning the lever handle 94 in the opposite direction and causing pin 96 to be inserted within one of the holes 98, the tongue 66 and head rest cushions 26 thereon, can selectively be fixed in a horizontal position as shown or one of the other stop positions as provided by the holes 98.

Figure 6:
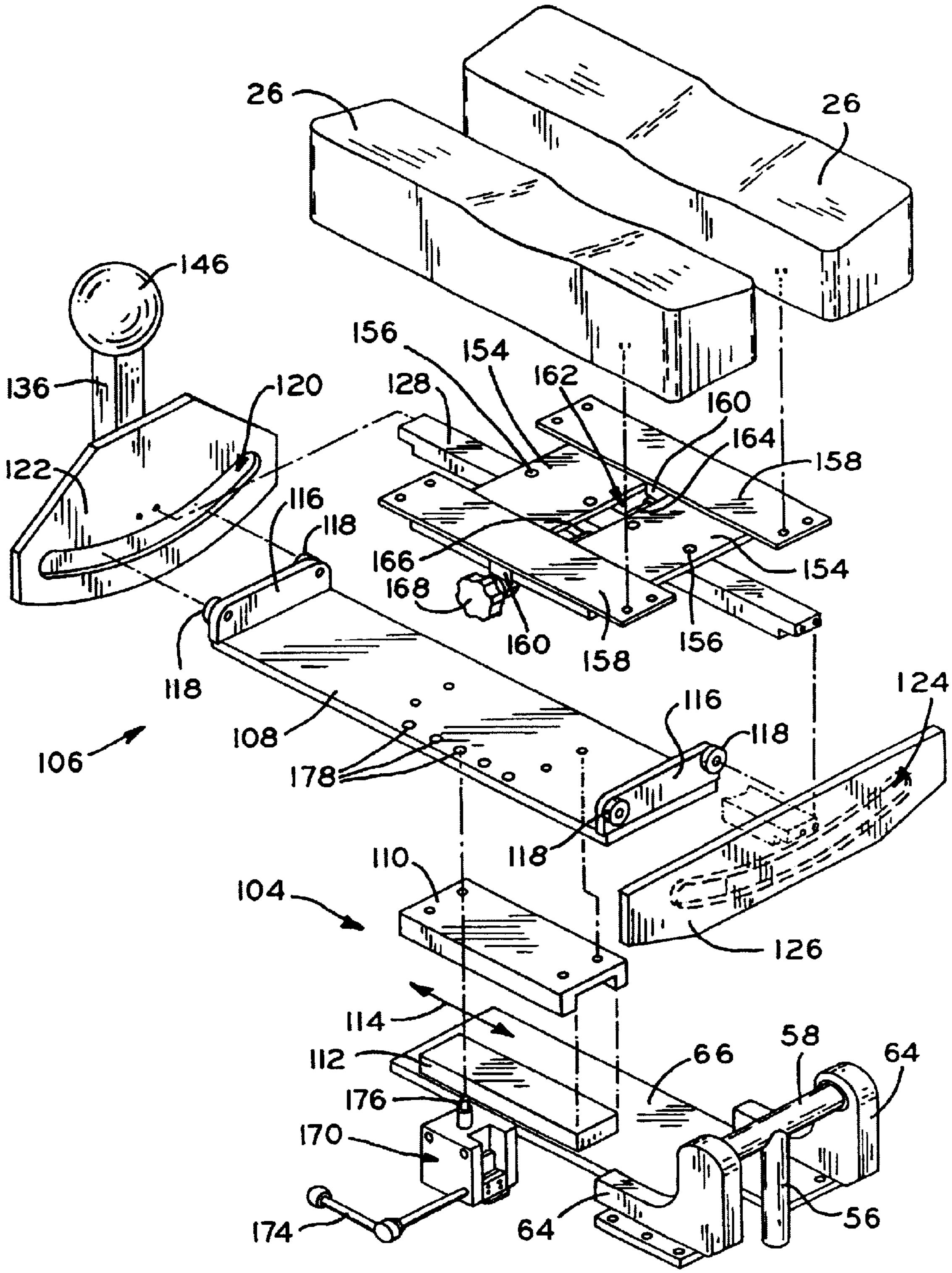
FIG. 6 is a perspective exploded view of the cradle portion of the head support section adapted for longitudinal sliding motion in accordance with the principles of the present invention.

A slide block 104 is provided on the tongue 66 and slidingly supports a cradle generally designated by the numeral 106 whereupon the head rest cushions 26 are supported. Cradle 106, as best seen in FIG. 6, includes a base plate 108 affixed to the upper slide member 110 of slide block 104 with screws as shown or other suitable means. The upper slide member 110 fits over the lower slide member 112 which is affixed to the tongue 66 by screws as shown or other suitable means. The aligned upper and lower slide members 110 and 112 are selectively moveable parallel with one another in a direction generally indicated by arrows 114. Accordingly, since upper slide member 110 is affixed to the base plate 108 of cradle 106 and the lower slide member 112 is affixed to the tongue 66, the cradle 106 is selectively slidingly moveable horizontally and, as shown, longitudinally in the direction of arrows 114 or also longitudinally along the treatment table longitudinal axis. Anti-friction bearings are provided between the upper and lower slide members 110 and 112 for thereby providing generally "frictionless" sliding motion therebetween. Further, the upper and lower slide members 110 and 112 are engaged with one another with tracks which prevent disengagement and only allow parallel sliding motion therebetween. In this manner, once the upper and lower slide members 110 and 112 are engaged, the cradle 106 is prevented from being removed from tongue 66 and is allowed only to slidingly move along the longitudinal axis of the treatment table as depicted by arrows 114. It is noted that in the preferred embodiment, the slide block 104 is a linear motion component manufactured and provided by Tusk Direct, Inc., of Bethel, Conn.

Figure 7:
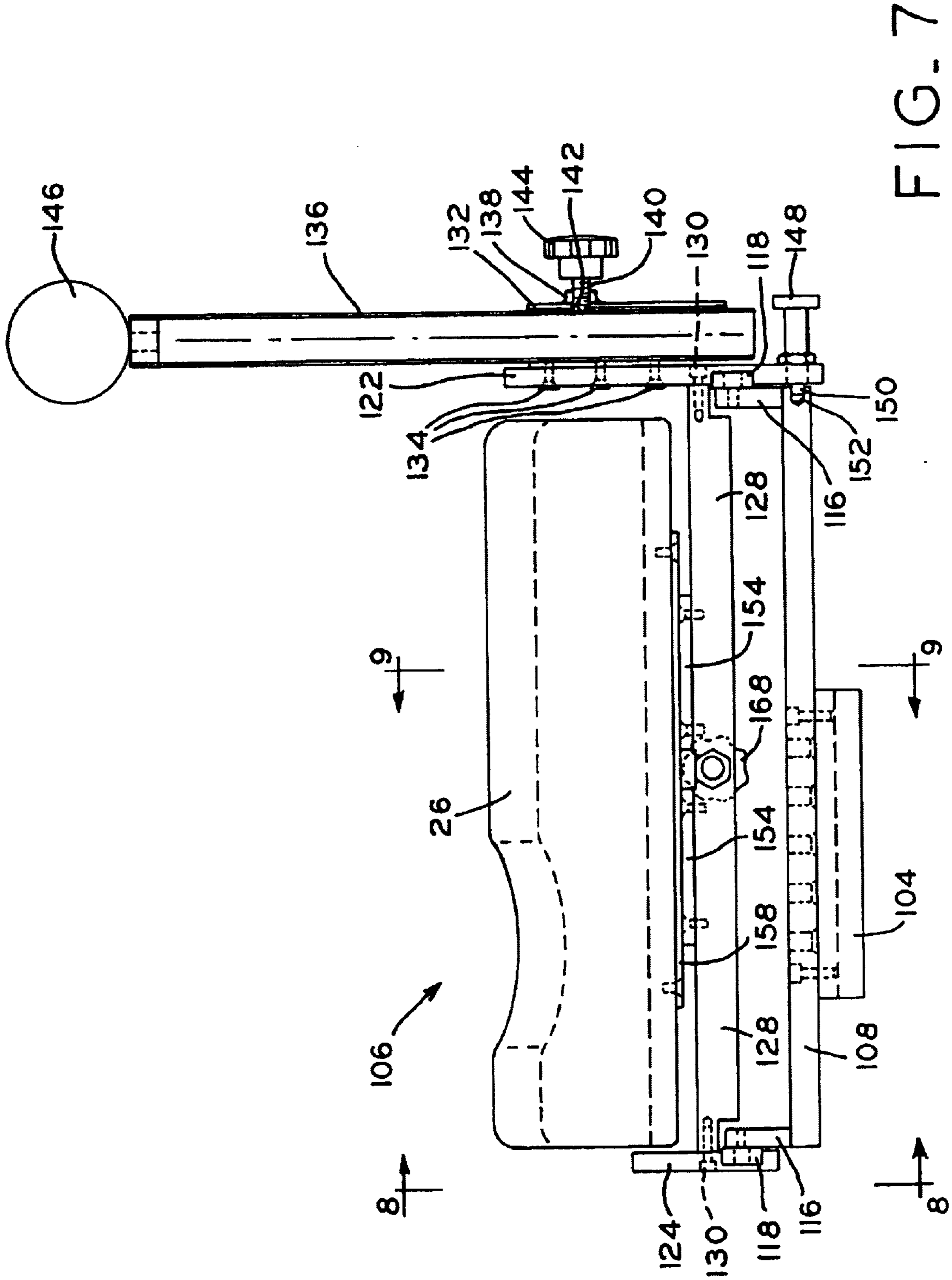
FIG. 7 is a side elevation view of the cradle shown in FIG. 6.
Figure 8:
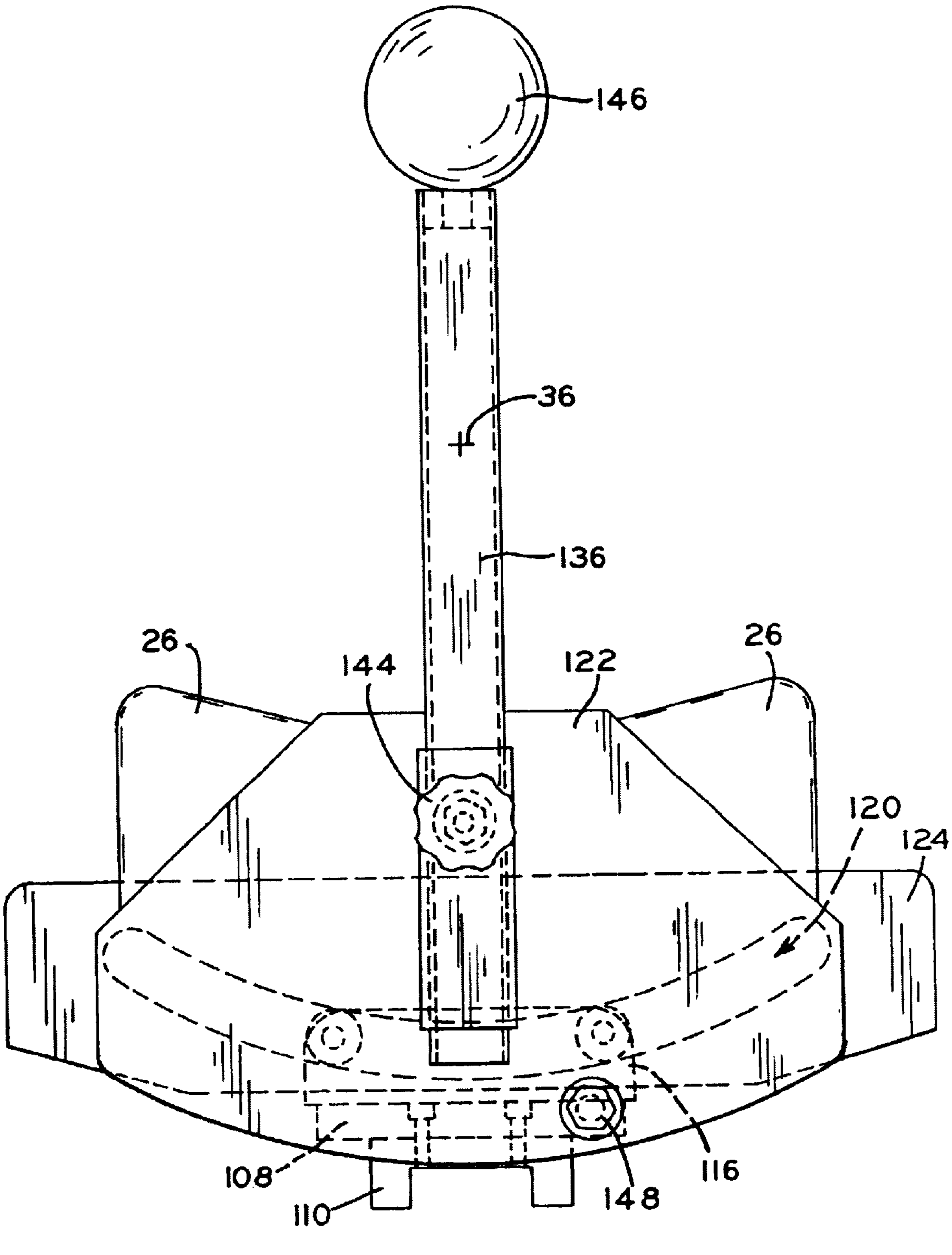
FIG. 8 is a rear view of the cradle shown in FIG. 7 and taken generally along line 8—8.
Figure 9:
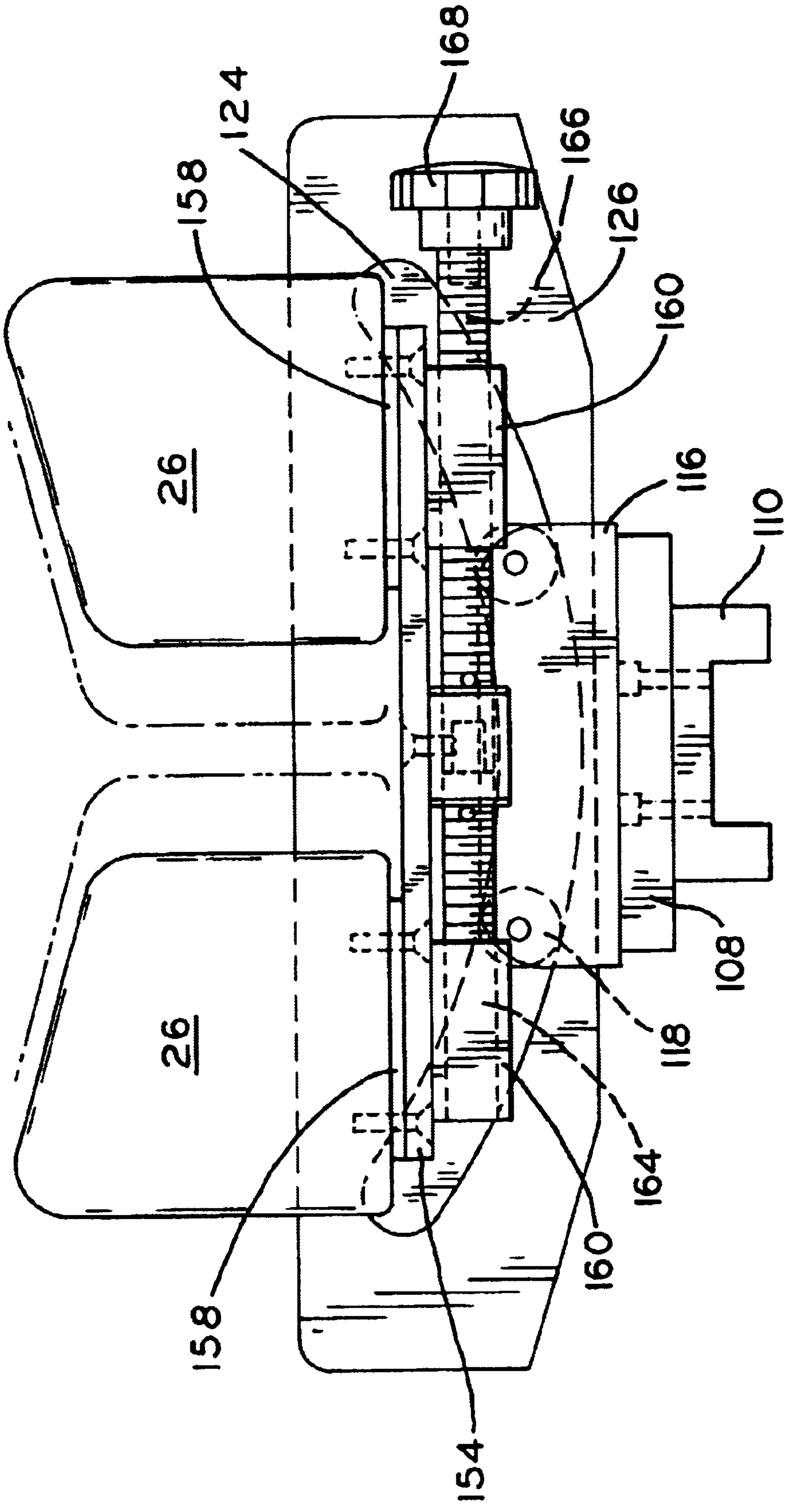
FIG. 9 is a cross-sectional view of the cradle shown in FIG. 7 and taken generally along line 9—9.
Figure 10:
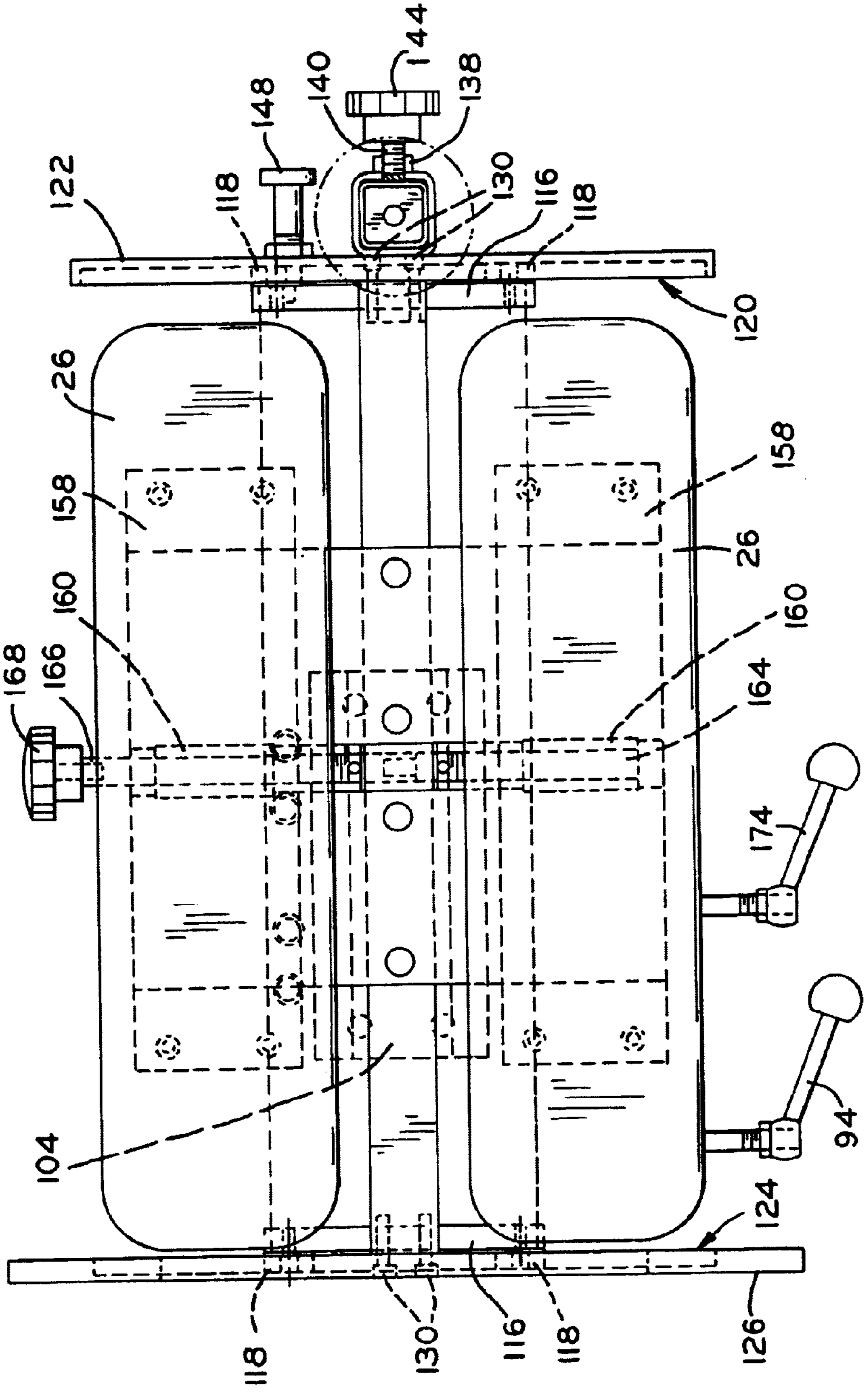
FIG. 10 is a top plan view of the cradle shown in FIG. 7.

At each longitudinal end of base plate 108 there are provided ears 116. Rollers 118 are rotatably mounted to ears 116 as shown. The rollers at one end of base plate 108 are adapted to be received within a curvilinear slot 120 of handle plate 122, whereas the rollers, 118 at the other end of base plate 108 are adapted to be received within curvilinear slot 124 of inner plate 126. Handle plate 122 and inner plate 126 are attached to one another via longitudinal head rest support beam 128 extending therebetween. As best seen in FIG. 7, support beam 128 is affixed to the handle plate 122 and inner plate 126 via screws 130. As should now be appreciated, head rest support beam 128 along with the head rest cushions 26 and plates 122 and 126 are selectively pivotable about the longitudinal axis 36 in view of plates 122 and 126 being captured on and sliding over the rollers 118 within respective curvilinear slots 120 and 124. Essentially, the axial center of curvilinear slots 120 and 124 is longitudinal axis 36.

Referring now more particularly to FIG. 7, a square tube 132 is attached to handle plate 122 with screws 134. Square handle 136 is slidingly received within tube 132. Nut 138 is affixed to tube 132 and threaded rod 140 is threadingly received therethrough and extends through a hole 142 for selectively frictionally engaging handle 136. Knob 144 is affixed to the end of threaded rod 140 whereby threaded rod 140 can selectively be turned for frictionally engaging and disengaging handle 136. Knob 146 is affixed to the upper end of handle 136 for grasping and using handle 136. Thus, the length of handle 136 extending out of tube 132 is selectively adjustable and, because tube 132 is affixed to handle plate 122, the cradle 106 and essentially support beam 128 and the head rest cushions 26 thereon can be selectively rocked or pivoted about the longitudinal axis 36 by grasping and laterally manipulating knob 146 and handle 136.

At the lower end of handle plate 122, there is provided a push/pull knob 148 affixed to pin 150. Accordingly, by pushing or pulling knob 148, pin 150 is selectively inserted or retracted from hole 152 extending into base plate 108. In this manner, cradle 106 can selectively be affixed to the base plate 108 preventing rotational motion about longitudinal axis 36 or, in the alternative, released for allowing such rotational motion about longitudinal axis 36 and providing rotation to a patient's spine.

Nylon plates 154 are affixed to support beam 128 using screws 156. Head rest cushion support plates 158 are also preferably made of nylon and are slidingly received over nylon plates 154. Head rest cushions 26 are each attached to a respective cushion support plate 158 with screws or other suitable means. Blocks 160 are affixed to the underside of head rest cushion support plates 158 and are received within the elongate opening 162 between the nylon plates 154. Threaded rods 164 and 166 are collinearly coupled or attached to one another and are threadingly received within threaded bores in blocks 160. At one end of threaded rod 160 a turn knob 168 is provided for selectively turning threaded rods 164 and 166. A stop is provided at the support beam 128 preventing threaded rods 164 and 166 from longitudinal movement thereof but allowing rotation when turned by the knob 168. Threaded rods 164 and 166 as well as their respective threaded bores within blocks 160 are reverse threaded with respect to one another so that, upon turning of knob 168, blocks 160 as well as the plates 158 and cushions 26 thereon will travel in opposite direction with respect to one another. Accordingly, by merely turning knob 168, the distance between cushions 26 is selectively adjustable for accommodating the face of the patient.

Figure 11:
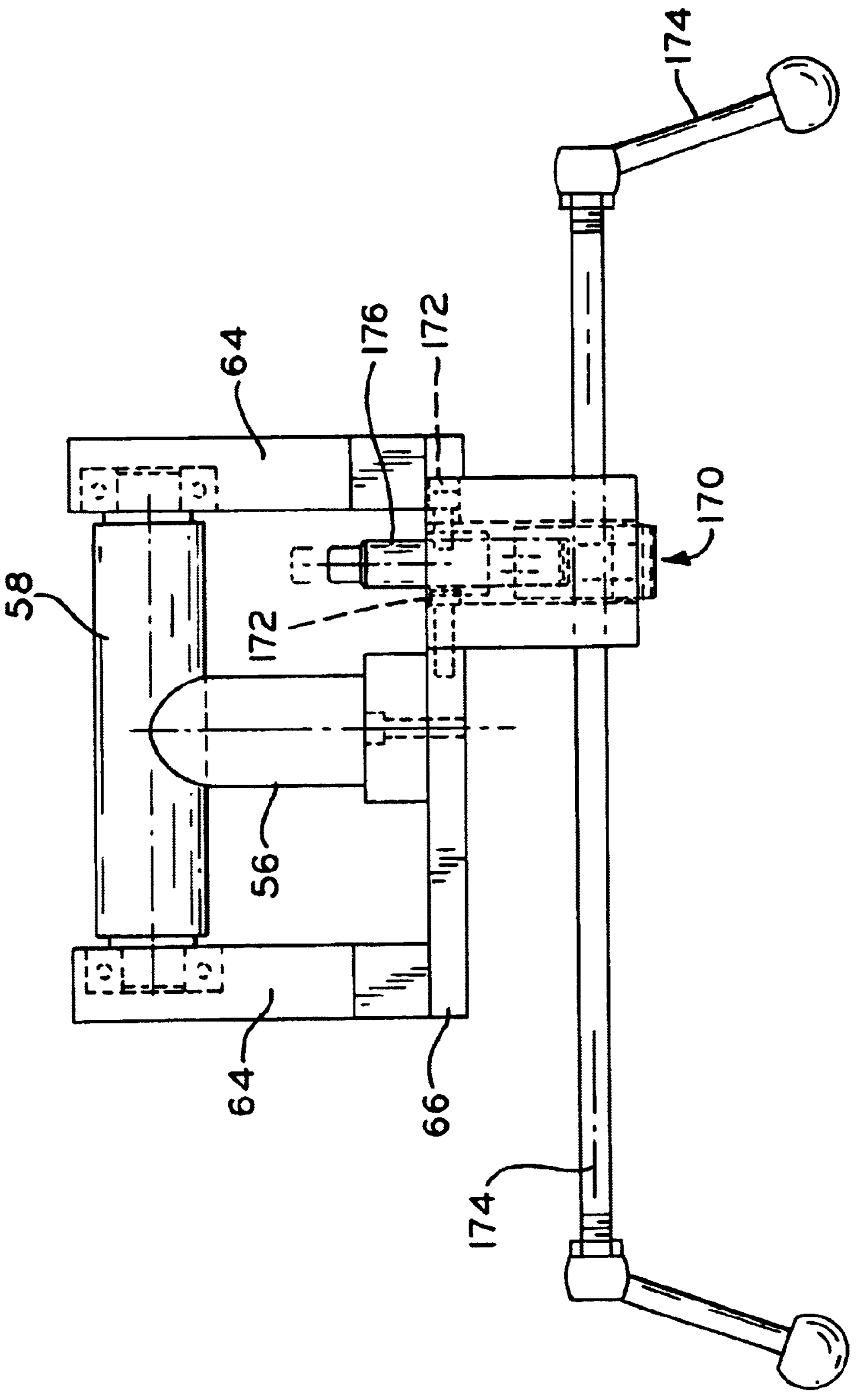
FIG. 11 is a cross-sectional view taken generally along line 11—11 of FIG. 3.

Referring now more particularly to FIGS. 6 and 11, a cam mechanism 170 is provided and affixed to the tongue 66 with screws 172. Lever handle 174 is provided and cooperates with cam mechanism 170 for selectively causing pin 176 to be moved vertically up and down. Pin 176 is adapted to be received within any one of the holes 178 extending through the base plate 108 of the cradle 106. Accordingly, by selectively inserting pin 176 within any one of the adjustment holes 178, the slide block members 110 and 112 are prevented from longitudinal sliding motion relative to one another and cradle 106 is affixed thereby also preventing longitudinal motion thereof. However, by retracting pin 176 from the holes 178, frictionless sliding motion is allowed to occur between slide block members 110 and 112 thereby allowing the chiropractor to grasp handle knob 146 and selectively longitudinally move the cradle 106 as desired or needed and with practically no friction or drag. As should now also be appreciated, by selectively also releasing lever handles 52, 94 and/or push/pull knob 148 and by merely grasping handle knob 146, the chiropractor can combine true longitudinal distraction wherein cradle 106 is longitudinally slidingly moved as indicated by arrows 114 with vertical flexion about horizontal axis 32 extension also about the horizontal axis 32, lateral flexion about the vertical axis 34, as well as rotation about the longitudinal axis 36.

Figure 12:
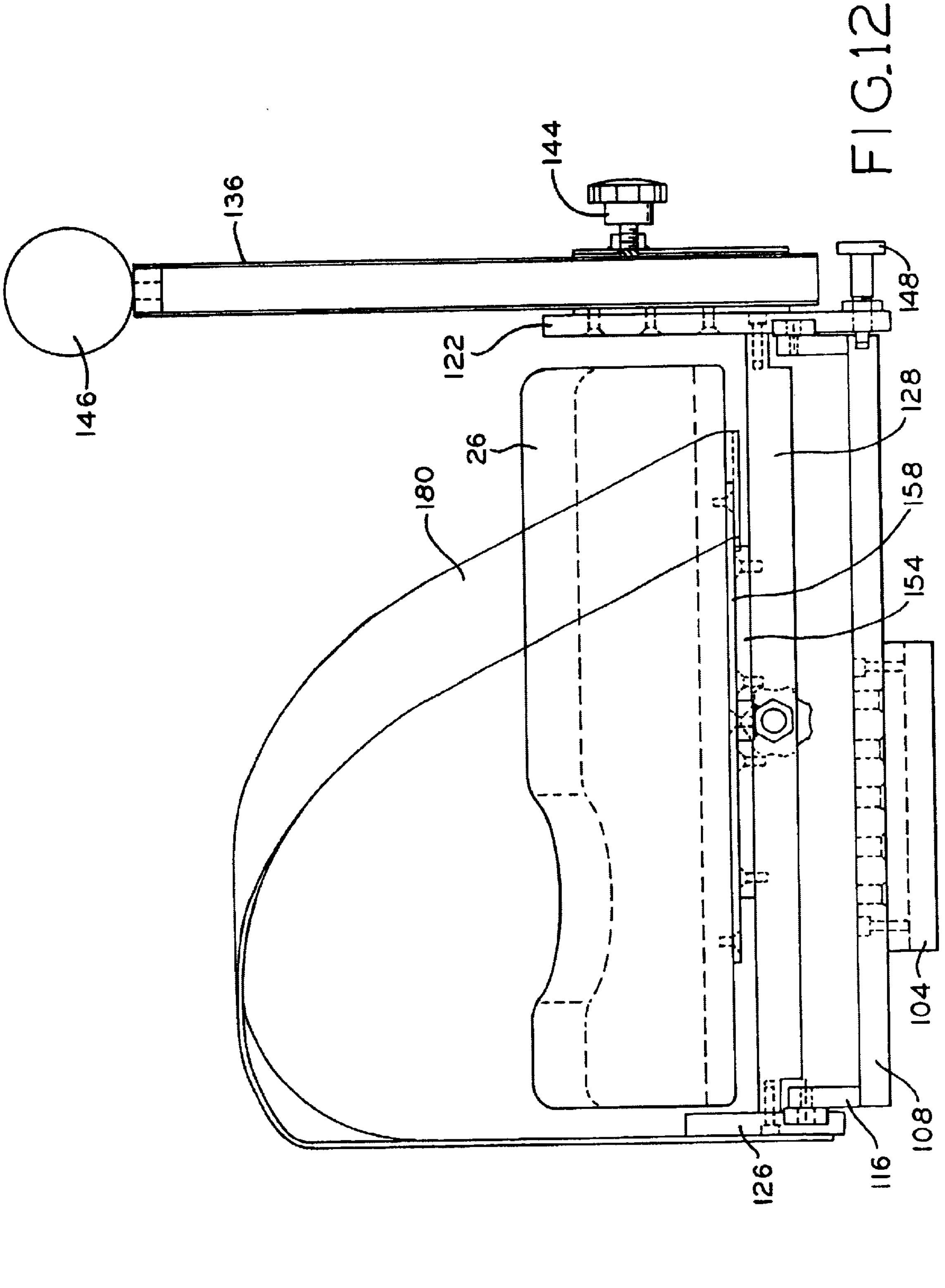
FIG. 12 is a side view of the cradle showing the occipital restraint according to the present invention; and, FIG. 13 is a top plan view of the cradle shown in FIG. 12.
Figure 13:
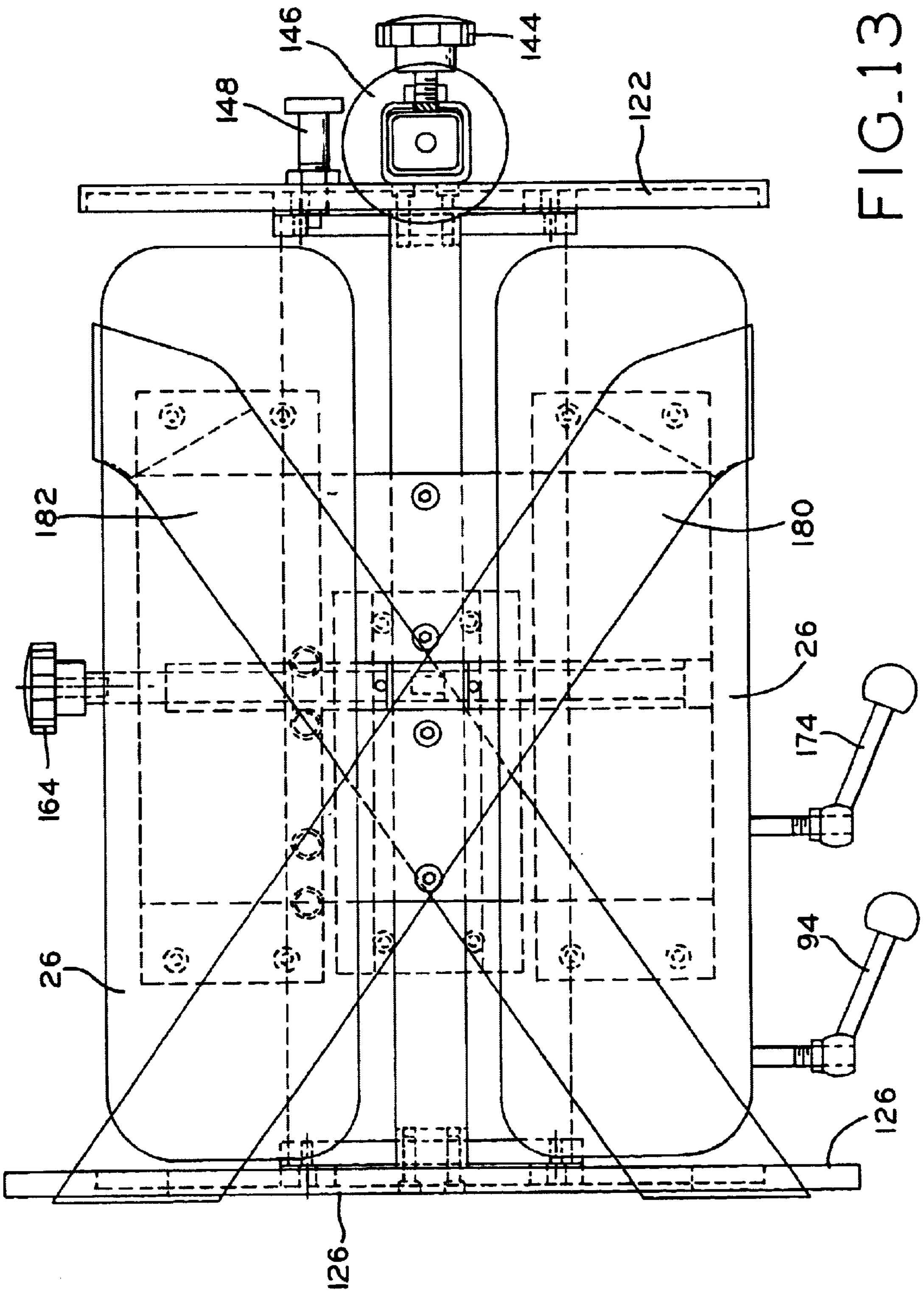

For restraining a patient's head upon the head rest cushions 26, as shown in FIGS. 12 and 13, occipital straps 180 and 182 are provided and affixed at one end to the underside of support plates 158 and are selectively detachably attached to the inner plate 126 at their other end preferably with complementary pile and loop fastening material on the respective inner plate 126 and the straps 180 and 182. After a patient is placed on the treatment table with their face placed downwardly upon the head rest cushions 26, the occipital restraint straps 180 and 182 are selectively placed over the patient's head for thereby restraining the patient's head thereon as may be desired or needed by the chiropractor.

When using the treatment table 10 the chiropractor controls the various headpiece or cradle 106 motions by selectively locking and releasing: lock or lever handle 52 for lateral flexion; lock or lever handle 94 for vertical flexion and extension; push/pull knob or lock 148 for rotation; and, lock or lever handle 174 for axial distraction. The headrest cushions are adjusted relative to one another using turn knob 168 and the patient lies with the eyes in the cushion relief cutout and the C5–C6 level of the spine located at the opening between the cervical or head support section 18 and the thoracic section or body support section 16 of the table or instrument 10. The following procedure is thereafter preferably used.

1. Tolerance Testing

Prior to application of distraction adjusting, patient tolerance to the procedure is to be tested. This need not be done every treatment, but prior to first adjusting the patient and at any time a new procedure is added to the adjustment so as to establish patient tolerance.

A. Tolerance Testing for Application of Axial Distraction of the Cervical Spine:

1) The weight of the patient's head is used as the traction force as the headpiece is moved cephalward so as to apply traction to the cervical and upper thoracic spine. The patient is asked to report any sign of arm discomfort or pain in the spine or spasm of paravertebral muscles.

2) The above A(1) procedure is repeated as the doctor contacts and holds the posterior arch of each vertebrae to be tested so as to increase the axial distraction pull as the headpiece is moved cephalward. The patient is asked to report any sign of arm discomfort or pain in the spine or paravertebral muscles. Tenderness under the doctor's contact hand at the spinous process is common and requires a contact with light enough pressure so as to minimize any discomfort.

3) The above A(1) procedure is repeated as the doctor contacts and lifts the posterior arch of the spinal segments to be tolerance tested so as to apply increased cephalward stretch as the doctor's other hand moves the headpiece forward. The doctor feels the tautening of the posterior muscles and ligaments of the spinal segment being tested as the forward distraction is applied and the doctor asks the patient to report any sign of arm or spine discomfort. Again, tenderness at the spinous process contact may be present and necessitate a lighter contact for patient comfort.

4) The occipital lift or restraint straps 180 and 182 are placed on the patient's head and tested with the procedures of A(1), A(2) and A(3).

B. Tolerance Testing for Application of Flexion of the Cervical Spine:

1) The lever lock 94 is released and the weight of the patient's head is used as the flexion force as the headpiece is moved downward so as to apply flexion to the cervical and upper thoracic spine. The patient is asked to report any sign of arm discomfort or pain in the spine or spasm of paravertebral muscles.

2) The procedure of B(1) is repeated as the doctor contacts the posterior arch of each vertebrae from C1 to T9 as flexion is applied with the patient's head weight as the traction force. The patient is asked to report any sign of arm discomfort or pain in the spine or paravertebral muscles. Tenderness under the doctor's contact hand at the spinous process is common and requires a contact with light enough pressure as to minimize any discomfort.

3) The procedure of B(1) is repeated as the doctor contacts and stabilizes the posterior arch of the spinal segments to be tolerance tested and applies a cephalward stretch as the doctor's other hand moves the headpiece downward into flexion. The doctor feels the tautening of the posterior muscles and ligaments of the spinal segment being tested as the flexion is applied and the doctor asks the patient to report any sign of arm or spine discomfort. Again, tenderness at the spinous process contact may be present and necessitate a lighter contact for patient comfort.

4) The occipital lift or restraint straps 180 and 182 are placed on the patient's head and with flexion motion tested repeating the procedures of B(1), B(2) and B(3).

It is noted that Lateralization of pain into the upper extremity or discomfort at any spine area or paravertebral muscles or ligaments indicates an aggravation of tissues and the technique needs to be applied at a lesser amplitude and/or duration for patient comfort. The technique described is always to be applied below patient tolerance. For example, if there is no pain when using the head as a traction force as the doctor contacts the spinous process, but the use of the occipital restraint aggravates the spinal pain or the patient complains of creating a new pain, the doctor would start with the treatment not utilizing the occipital restraint until such time as it does not cause discomfort to tolerance testing.

Additionally, lateral flexion, circumduction, rotation, and extension motions of the cervical spine are tested for tolerance by slowly performing them and asking the patient if they feel pain. The technique is applied well below an amount of motion or distraction that causes any pain or muscle irritation.

It is further noted that the following summary of facts is important in cervical spine distraction adjusting:

1. In all headpiece use, the doctor controls the amplitude, frequency, and time of spinal adjustment, always treating within patient tolerance as found in tolerance testing. Discomfort at any spine level during distraction adjusting of the cervical spine necessitates less distraction application until no discomfort is felt.
2. Long Y-axis or true longitudinal distraction along the table longitudinal axis can be applied alone or combined with flexion, lateral flexion, circumduction, rotation, and extension motions of the cervical spine.
3. Occipital Lift Assist use is by doctor preference and tolerance testing result.
4. Two methods of headpiece use in applying axial distraction with or without the range of motion adjustment procedures of flexion, extension, lateral flexion, rotation, and circumduction are available:
   A. Free floating headpiece: Here the doctor moves the headpiece as it applies distraction; and,
   B. Fixed headpiece: Here axial distraction of the headpiece is fixed as the doctor applies distraction 2. Patient Adjustment Procedures when Radiculopathy of Upper Extremity is Present:

Herniated cervical disc or stenosis due to bone hypertrophy of the foraminal nerve root opening is commonly involved in the radiculopathy patient. Only axial distraction with or without flexion added is used in treating the radiculopathy patient.

Application of Axial Distraction with or without Flexion Added for Radiculopathy Patient Adjusting:

A. Axial distraction can be applied using head weight alone as the traction force as in procedure A(1) above, with doctor contact of the posterior arch of each vertebra as in procedure A(2) above, with doctor assisted cephalward contact on the spinous process at the level of desired spinal segment distraction as in procedure A(3) above, or with the occipital lift assist in place as in procedure A(4) above. The tolerance testing for each of these procedures determines which axial distraction application is used.

B. Flexion can be added to the cervical spine as tolerated by the patient when tested as in procedures B(1) to B(4) above. This flexion angle is the angle that relieves, and does not aggravate patient symptoms, and may be preset or added simultaneously with axial distraction. The occipital restraint is used if no discomfort for patient occurs. Flexion alone or with axial distraction may be the best adjustment setup for some patients. The doctor determines the flexion and axial distraction amount by patient response and relief. Tolerance testing directs application of the technique.

Three sets of twenty-second distraction sessions are applied to the patient with radicular symptoms. Each 20-second session consists of 5 four-second distraction/flexion combined motions to the involved spinal level.

3. Patient Adjustment Procedures when No Radiculopathy is Present:

Patients with neck pain that may be associated with shoulder and upper arm discomfort that is not dermatomal in nature, are treated with distraction adjustment of the intervertebral disc and facet joints at single or multiple levels of the cervical or thoracic spine. The indications for this procedure are patients with pain in the cervical and thoracic spine due to degenerative disc disease, facet subluxation, facet arthrosis, stiffness, pain, difficulty in applying typical thrust adjustments, loss of range of motion, whiplash type injuries, headache, suboccipital tightness, upper thoracic spine tightness, osteoporosis not allowing thrust adjustment, certain post surgical spines, some ankylosis patients, and patients needing relief of muscle spasm, adhesion, pain, and loss of mobility before any other adjustment technique can be performed.

A. Axial distraction as in procedures A(1) to A(4) is combined with flexion as in procedures B(1) to B4) in tolerance testing. Tolerance testing is applied prior to using each adjustment procedure and the type and amount of axial distraction is selected from the results of these tests.

B. Lateral flexion is applied to a specific spinal level by first placing the segment into axial flexion distraction, and while isolating the segment in this position, lateral flexion is added. The doctor's contact hand on the spine will stabilize the motion segment below the segment to be placed into axial distraction and flexion; that is, if the C6 posterior arch is contacted, the C5–C6 facet joints will be adjusted in this set up.

C. Circumduction is applied by coupling the motions of axial flexion and lateral flexion, starting from the neutral horizontal axis and moving the facets through the range of motion that is comfortable and slightly beyond the taut point or elastic resistance of the joint capsule. Cavitation of the facet joints may be felt or heard in these movements.

D. Rotation is applied by contacting the posterior arch below the spinal segment to be rotated; that is, if rotation the C5–C6 facet joints, the C6 arch is contacted and stabilized. Axial flexion distraction is applied, followed by rotation.

E. Extension is applied by stabilizing the posterior arch of the vertebra below the spinal segment to be extended; that is, if extending the C5 segment, stabilization of the C6 posterior arch is applied. Extension of the cervical spine is performed by slowing bringing the headpiece into extension.

It is noted that all of the above ranges of motion are patient tolerance tested prior to executing the movement. The same rules apply for these ranges of motion that do for the above tests, namely always follow the patient response and treat below any pain production.

Thoracic Spine Distraction Adjustment Procedures

1. Thoracic Disc Herniation:

The technique for cervical spine disc herniation is utilized in thoracic disc herniation, including tolerance testing. Remember to contact the posterior arch below the disc to be distracted; that is, if MRI proves a T7–T8 disc herniation, the contact by the doctor is the posterior arch of T8 as distraction is applied for three 20-second pumps. Each 20-second pumping adjustment consists of 5 four second pumping motions.

2. Upper Thoracic Spine Pain and Loss of Range of Motion:

Here, the upper four to six thoracic segments are laterally flexed and then flexed and extended. This combined adjustment procedure returns range of motion, relieves muscle tightness and allows for high velocity, low amplitude thrust adjustments to be given more easily. Often the patient is too resistant to allow such adjustment with this adjustment procedure being given first This is very comforting the common upper thoracic tightness and headache and shoulder pain patient.

3. Rotation for Scoliosis of the Cervico-thoracic Spine

The cervical headpiece is placed in rotation so as to derotate the convex curve of the scoliosis and axial distraction with lateral flexion into the convexity of the curve is administered.

4. Foramen Magnum Pump

Contacting the occiput is followed with axial distraction of the spine. This can be performed by the doctor contacting the occiput and applying the distraction, or place the occipital lift system in place and contact specific spinal segments to produce axial distraction from that level cephalward. This is a relaxation type adjustment or preparation prior to the other adjustment procedures explained here.

While the invention has been described as having specific embodiments, it will be understood that it is capable of further modifications. This application is, therefore, intended to cover any variations, uses, or adaptations of the invention following the general principles thereof and including such departures from the present disclosure as come within known or customary practice in the art to which this invention pertains and fall within the limits of the appended claims.

What is claimed is:

1. A method of treating a patient's spine on a treatment table including a first portion adapted to support a patient's body and a second portion adapted to support the patient's head, wherein the second portion is selectively freely movable on an anti friction structure relative to the first portion along a longitudinal axis, said method comprising the steps of:

supporting the patient with the patient's body resting on the first table portion and the patient's head resting on the second table portion; and, selectively longitudinally moving the second table portion on the anti friction structure and the patient's head thereon, thereby selectively providing distraction to the patient's spine in a direction generally along the table longitudinal axis.

2. The method of claim 1 wherein the second table portion is pivotable about a horizontal axis transverse to the longitudinal axis, and further wherein the patient's head is moved in a direction downwardly or upwardly pivoting about the horizontal axis, thereby selectively placing the patient's spine in flexion or extension.

3. The method of claim 1 wherein the second table portion is pivotable about a vertical axis transverse to the longitudinal axis, and further wherein the patient's head is moved laterally pivoting about the vertical axis, thereby selectively placing the patient's spine in lateral flexion.

4. The method of claim 1 wherein the second table portion is pivotable about the longitudinal axis, and further wherein the patient's head is simultaneously pivoted about the longitudinal axis, thereby selectively placing the patient's spine in rotation.

5. The method of claim 1 wherein said step of selectively longitudinally moving includes first testing the patient's tolerance for discomfort by longitudinally moving the second table portion with only the weight of the patient's head thereon.

6. The method of claim 5 wherein the patient's tolerance is further tested by applying an occipital downward force on the patient's head while simultaneously longitudinally moving the table second portion thereby increasing the axial distraction force applied to the patient's spine.

7. The method of claim 6 wherein the table second portion includes an occipital restraint and said occipital downward force is provided by restraining the patient's head on the table second portion with the occipital restraint.

8. The method of claim 1 wherein the second table portion is pivotable about a horizontal axis transverse to the longitudinal axis and about a vertical axis transverse to the longitudinal axis, and further wherein the patient's head is simultaneously moved downwardly pivoting about the horizontal axis and laterally pivoting about the vertical axis, thereby selectively placing the patient's spine in circumduction.

9. The method of claim 1 wherein, during the step of supporting, said patient is supported in a generally horizontal face down position with at least a portion of the patient's face resting on the table second portion.

10. The method of claim 1 wherein said table second portion includes an occipital restraint and said method further includes the step of restraining the patient's head with the occipital restraint during said step of selectively longitudinally moving.

11. The method of claim 1 wherein, during said step of selectively longitudinally moving, one of the patient's body or spinal segments are selectively retained away from the patient's head thereby selectively increasing the distraction to the patient's spine.

12. The method of claim 11 wherein the table second portion includes a handle, and wherein said second support portion is selectively longitudinally moveable by grasping and moving the handle.

13. The method of claim 12 wherein said table second portion includes an occipital restraint and said method further includes the step of restraining the patient's head with the occipital restraint during said step of selectively longitudinally moving.

14. The method of claim 1 wherein the table second portion includes a handle, and wherein said second support portion is selectively longitudinally moveable by grasping and moving the handle.

15. A treatment table for treating a patient's spine while being supported in a generally face down horizontal position, said treatment table comprising:

a first support portion supporting a patient's body;

a second support portion supporting a patient's head and being spaced apart from said first support portion along a longitudinal axis; and, wherein said second support portion is supported on an anti friction structure whereby said second support portion is selectively freely moveable relative to said first support portion along said longitudinal axis.

16. The treatment table of claim 15 further comprising a handle mounted to said second support portion whereby said second support portion is moveable along said longitudinal axis.

17. The treatment table of claim 15 wherein said second support portion is pivotally attached to said first support portion for pivotal motion about a horizontal axis transverse to said longitudinal axis.

18. The treatment table of claim 15 wherein said second support portion is pivotally attached to said first support portion for pivotal motion about a vertical axis transverse to said longitudinal axis.

19. The treatment table of claim 15 wherein said second support portion is pivotally attached to said first support portion for pivotal motion about said longitudinal axis.

20. The treatment table of claim 15 wherein said anti friction structure includes a slide block mounted between said first support portion and said second support portion.

21. The treatment table of claim 15 further comprising an occipital restraint on said table second portion whereby a patient's head can selectively be restrained thereon.

22. The treatment table of claim 15 further comprising a stop mechanism selectively engaging said table second portion and selectively preventing longitudinal movement thereof relative to said table first support portion.

23. The treatment table of claim 15 wherein said second support portion is pivotally attached to said first support portion for pivotal motion about a horizontal axis transverse to said longitudinal axis, for pivotal motion about a vertical axis transverse to said longitudinal axis, and for pivotal motion about said longitudinal axis.

24. The treatment table of claim 15 further comprising a handle mounted to said second support portion whereby said second support portion is moveable along said longitudinal axis, an occipital restraint on said table second portion whereby a patient's head can selectively be restrained thereon, and a stop mechanism selectively engaging said table second portion and selectively preventing longitudinal movement thereof relative to said table first support portion.

25. A treatment table for treating a patient's spine while being supported in a generally face down horizontal position, said treatment table comprising:

a first support portion supporting a patient's body;

a second support portion supporting a patient's head and being spaced apart from said first support portion along a longitudinal axis; and, wherein said second support portion is supported on anti friction means for allowing generally free motion of said second support portion relative to said first support portion along said longitudinal axis.

26. The treatment table of claim 25 wherein said second support portion is pivotally attached to said first support portion for pivotal motion about a horizontal axis transverse to said longitudinal axis, for pivotal motion about a vertical axis transverse to said longitudinal axis, and for pivotal motion about said longitudinal axis.

27. The treatment table of claim 25 further comprising a handle mounted to said second support portion whereby said second support portion is moveable along said longitudinal axis, an occipital restraint on said table second portion whereby a patient's head can selectively be restrained thereon, and a stop mechanism selectively engaging said table second portion and selectively preventing longitudinal movement thereof relative to said table first support portion.

28. In a treatment table for treating a patient's spine while being supported in a generally face down horizontal position, said treatment table including a first support portion supporting a patient's body and a second support portion supporting a patient's head and being spaced apart from said first support portion along a longitudinal axis, an improvement wherein said second support portion is supported on an anti friction structure whereby said second support portion is selectively freely moveable relative to said first support portion along said longitudinal axis and whereby the patient's spine can selectively be placed in distraction by selectively moving the table second portion longitudinally along said longitudinal axis on said anti friction structure.

29. The treatment table of claim 28 wherein said second support portion is pivotally attached to said first support portion for pivotal motion about a horizontal axis transverse to said longitudinal axis, for pivotal motion about a vertical axis transverse to said longitudinal axis, and for pivotal motion about said longitudinal axis.

30. The treatment table of claim 28 further comprising a handle mounted to said second support portion whereby said second support portion is moveable along said longitudinal axis, an occipital restraint on said table second portion whereby a patient's head can selectively be restrained thereon, and a stop mechanism selectively engaging said table second portion and selectively preventing longitudinal movement thereof relative to said table first support portion.

* * * * *